US011753356B2

(12) United States Patent
Kreischer et al.

(10) Patent No.: US 11,753,356 B2
(45) Date of Patent: Sep. 12, 2023

(54) METHODS FOR OPERATING ETHYLENE OLIGOMERIZATION REACTOR SYSTEMS WITH AN INTEGRATED ULTRASONIC FLOW METER

(71) Applicant: Chevron Phillips Chemical Company LP, The Woodlands, TX (US)

(72) Inventors: Bruce E. Kreischer, Kingwood, TX (US); Kendall M. Hurst, Owasso, OK (US); Eric D. Schwerdtfeger, Bartlesville, OK (US); Steven M. Bischof, Humble, TX (US); Jared Fern, Kingwood, TX (US); Kent E. Mitchell, Bartlesville, OK (US); James Hillier, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 18/057,803

(22) Filed: Nov. 22, 2022

(65) Prior Publication Data
US 2023/0081124 A1 Mar. 16, 2023

Related U.S. Application Data

(63) Continuation of application No. 17/469,986, filed on Sep. 9, 2021, now Pat. No. 11,572,324.

(51) Int. Cl.
*C07C 2/32* (2006.01)
*B01J 8/10* (2006.01)
(Continued)

(52) U.S. Cl.
CPC .................. *C07C 2/32* (2013.01); *B01J 8/10* (2013.01); *B01J 8/1809* (2013.01); *B01J 8/1854* (2013.01);
(Continued)

(58) Field of Classification Search
CPC .... C07C 2/32; B01J 8/10; B01J 8/1809; B01J 8/1854; B01J 2208/00548;
(Continued)

(56) References Cited

U.S. PATENT DOCUMENTS 4,336,719 A * 6/1982 Lynnworth ............. G01F 1/002
73/861.31
4,742,472 A 5/1988 Sugimori
(Continued)

FOREIGN PATENT DOCUMENTS

EP 1348115 B1 4/2007
EP 2331825 B1 6/2017
(Continued)

OTHER PUBLICATIONS

International Search Report and Written Opinion issued in application No. PCT/US2022/042391 dated Dec. 22, 2022, 12 pp.
(Continued)

*Primary Examiner* — Ali Z Fadhel
(74) *Attorney, Agent, or Firm* — Merchant & Gould P.C.

(57) ABSTRACT

Methods for determining ethylene concentration in an ethylene oligomerization reactor using an ultrasonic flow meter are described, and these methods are integrated into ethylene oligomerization processes and related oligomerization reactor systems.

22 Claims, 4 Drawing Sheets

(51) Int. Cl.
*B01J 8/18* (2006.01)
*C12M 1/34* (2006.01)
*B01J 8/00* (2006.01)
*B01J 19/00* (2006.01)

(52) U.S. Cl.
CPC ............ *C12M 41/30* (2013.01); *C12M 41/32* (2013.01); *B01J 8/001* (2013.01); *B01J 19/0006* (2013.01); *B01J 19/0013* (2013.01); *B01J 2208/00548* (2013.01); *B01J 2208/00663* (2013.01)

(58) Field of Classification Search
CPC .............. B01J 2208/00663; B01J 8/001; B01J 19/0006; B01J 19/0013; C12M 41/30; C12M 41/32
See application file for complete search history.

(56) References Cited

U.S. PATENT DOCUMENTS

| | | | |
|---|---|---|---|
| 5,542,450 A | 8/1996 | King | |
| 6,460,412 B1* | 10/2002 | Cai | G01N 29/024 73/628 |
| 6,480,793 B1 | 11/2002 | Martin | |
| 6,612,186 B1 | 9/2003 | Patten | |
| 7,509,878 B2 | 3/2009 | Sato | |
| 7,942,067 B2 | 5/2011 | Araseki | |
| 8,071,389 B2 | 12/2011 | Weck | |
| 10,107,659 B2* | 10/2018 | Nagareda | G01F 15/18 |
| 10,908,010 B1* | 2/2021 | Barson | G01F 23/14 |
| 2002/0016494 A1* | 2/2002 | Yoneda | B01J 8/008 560/207 |
| 2002/0038160 A1* | 3/2002 | Maynard | G01N 29/30 700/109 |
| 2005/0011278 A1 | 1/2005 | Brown | |
| 2006/0241242 A1* | 10/2006 | Devlin | B01J 19/0093 525/53 |
| 2008/0058481 A1* | 3/2008 | Vandaele | B01J 19/2435 526/64 |
| 2008/0288182 A1* | 11/2008 | Cline | G01N 21/85 702/24 |
| 2013/0145816 A1 | 6/2013 | Lowe | |
| 2013/0171735 A1* | 7/2013 | Lawson | G01N 9/36 436/55 |
| 2015/0284303 A1 | 10/2015 | Zoricak | |
| 2016/0290849 A1 | 10/2016 | Badarlis | |
| 2016/0313160 A1* | 10/2016 | Ueberschlag | G01N 29/326 |
| 2017/0021328 A1 | 1/2017 | Darvas | |
| 2017/0022300 A1 | 1/2017 | Hirahara | |
| 2017/0102253 A1* | 4/2017 | Ye | G01F 15/00 |
| 2019/0242575 A1* | 8/2019 | Fisher | F23G 7/085 |
| 2019/0336934 A1 | 11/2019 | Hendrickson | |
| 2022/0032258 A1* | 2/2022 | Desai | C23C 16/4481 |
| 2022/0228930 A1* | 7/2022 | Hogendoorn | G01F 1/668 |

FOREIGN PATENT DOCUMENTS

| | | |
|---|---|---|
| WO | 2002052243 A1 | 7/2002 |
| WO | 2006082165 A1 | 8/2006 |
| WO | 2007074779 A1 | 7/2007 |
| WO | 2010040734 A1 | 4/2010 |
| WO | 2011078691 A2 | 6/2011 |
| WO | 2017113027 A1 | 7/2017 |

OTHER PUBLICATIONS

Henning et al. "In-line Concentration Measurement in Complex Liquids Using Ultrasonic Sensors." Ultrasonics, IPC Science and Technology Press LTD. Guildford, GB vol. 38, No. 1-8. Mar. 1, 2020. pp. 799-803.
J.P. Smith, et al., "Calculating the Speed of Sound in Natural Gas Using AGA Report No. 10," Jan. 2003, 11 pp.
Krohne BR Optisonic 3400-R01, Krohne, Jun. 2013, 16 pp.
Krohne Optisonic 3400 R03 Datasheet, Krohne, Feb. 2015, 52 pp.
L. Cavin, et al., "On-Line Conversion Monitoring Through Ultrasound Velocity Measurements in Bulk Styrene Polymerization in a Recycle Reactor Part II: Mathematical Model," Polymer Reaction Engineering, 8:3, Taylor & Francis Group, 2000, 225-240.
L. Cavin, et al., On-Line Conversion Monitoring Through Ultrasound Velocity Measurements in Bulk Styrene Polymerization in a Recycle Reactor. Part I: Experimental Validation, Polymer Reaction Engineering, 8:3, Taylor & Francis Group, 2000, 201-223.
Torbjorn Lofqvist, et al., "Speed of Sound Measurements in Gas Mixtures at Varying Composition Using an Ultrasonic Gas Flow Meter with Silicon Based Transducers," ResearchGate, Jan. 2003, 6 pp.

* cited by examiner

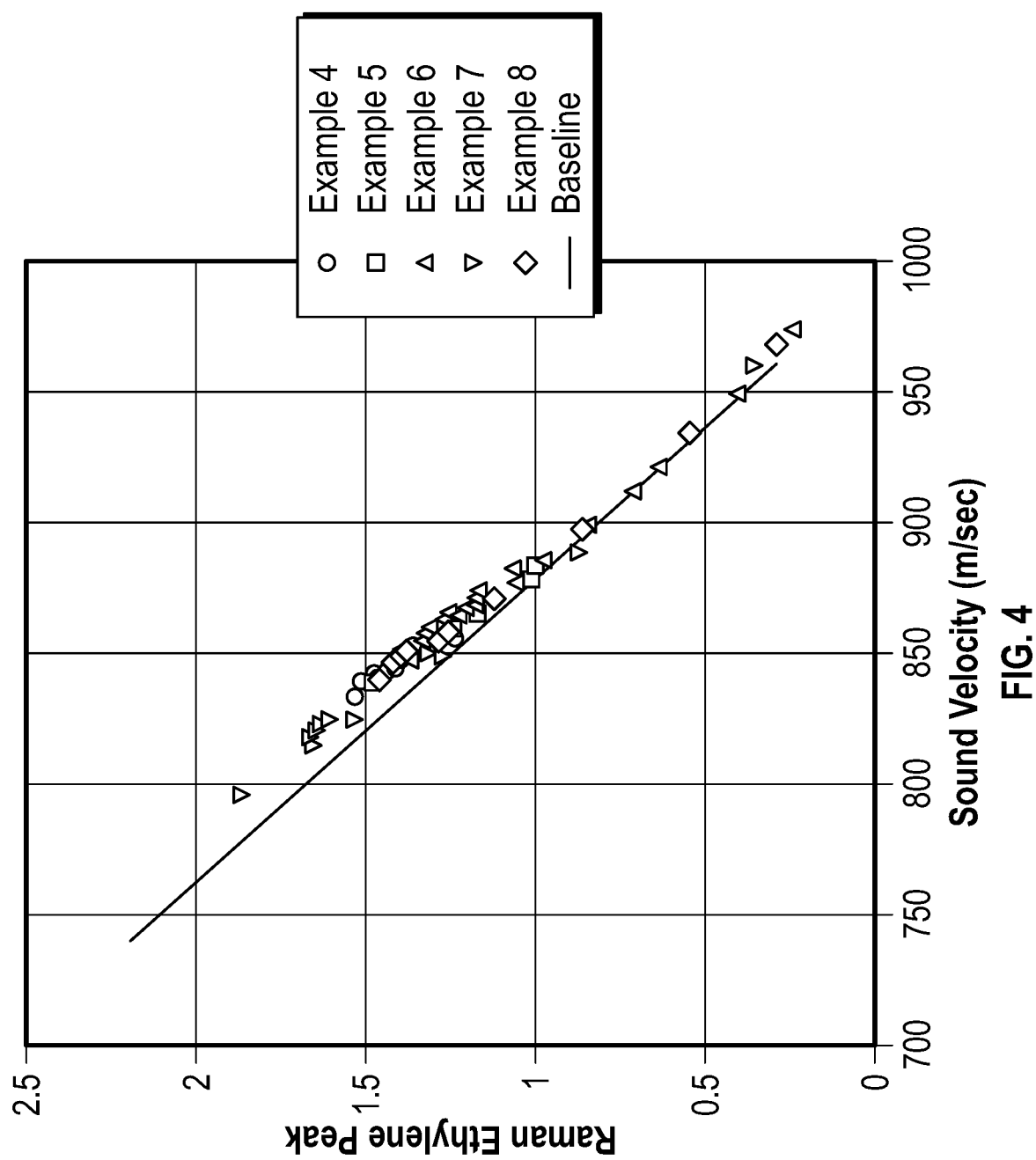

METHODS FOR OPERATING ETHYLENE OLIGOMERIZATION REACTOR SYSTEMS WITH AN INTEGRATED ULTRASONIC FLOW METER

REFERENCE TO RELATED APPLICATION

This application is a continuation application of U.S. patent application Ser. No. 17/469,986, filed on Sep. 9, 2021, now U.S. Pat. No. 11,572,324, the disclosure of which is incorporated herein by reference in its entirety.

FIELD OF THE INVENTION

The present disclosure concerns methods for determining the ethylene concentration in an ethylene oligomerization reactor using an ultrasonic flow meter, and the integration of these methods into related oligomerization processes and reactor systems.

BACKGROUND OF THE INVENTION

Chromium-based catalyst systems often are used for the continuous oligomerization of ethylene in a reactor to produce hexenes and/or octenes. However, many analytical techniques used to determine "real-time" ethylene concentration in the reactor, such as GC or IR or Raman spectroscopy, are problematic. Probes are used, which can foul or plug over time. Further, there are significant lag times in these analytical techniques. Thus, it would be beneficial to determine the real-time ethylene concentration using a technique that overcomes these drawbacks. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes for operating an oligomerization reactor system are disclosed herein. In accordance with an aspect of the present invention, a first process can comprise (I) contacting ethylene, an organic reaction medium, optionally hydrogen, and a catalyst system comprising a heteroatomic ligand chromium compound complex and an organoaluminum compound, or a heteroatomic ligand, a chromium compound, and an organoaluminum compound, in a reactor within the oligomerization reactor system to form an oligomer product, (II) discharging an effluent stream containing the oligomer product from the reactor through a reactor discharge line, (III) determining an ethylene concentration in the reactor, and (IV) adjusting an ethylene flow rate of the ethylene into the reactor, a catalyst system flow rate of the catalyst system into the reactor, a reaction temperature, a reaction pressure, or any combination thereof, when the ethylene concentration has reached a predetermined level. The ethylene concentration in the reactor can be determined by (i) flowing a reaction mixture through an ultrasonic flow meter integrated into the reactor, (ii) determining a speed of sound in the reaction mixture from the ultrasonic flow meter, and (iii) correlating the speed of sound to a standard to determine the ethylene concentration in the reactor.

In another aspect, a second process for operating an oligomerization reactor system is disclosed, and in this aspect, the process can comprise (I) contacting ethylene, an organic reaction medium, optionally hydrogen, and a catalyst system comprising a heteroatomic ligand chromium compound complex and an organoaluminum compound, or a heteroatomic ligand, a chromium compound, and an organoaluminum compound, in a reactor within the oligomerization reactor system to form an oligomer product, (II) discharging an effluent stream containing the oligomer product from the reactor through a reactor discharge line, (III) determining an ethylene concentration in the reactor discharge line, and (IV) adjusting an ethylene flow rate of the ethylene into the reactor, a catalyst system flow rate of the catalyst system into the reactor, a reaction temperature, a reaction pressure, or any combination thereof, when the ethylene concentration has reached a predetermined level. The ethylene concentration in the reactor discharge line can be determined by (i) flowing the effluent stream through an ultrasonic flow meter integrated into the reactor discharge line, (ii) determining a speed of sound in the effluent stream from the ultrasonic flow meter, and (iii) correlating the speed of sound to a standard to determine the ethylene concentration in the reactor discharge line.

A representative oligomerization reactor system consistent with aspects of this invention can comprise (A) a reactor configured to contact a catalyst system with ethylene, an organic reaction medium, and optional hydrogen under oligomerization conditions to produce an oligomer product, (B) one or more reactor inlets configured to introduce the catalyst system, ethylene, and the organic reaction medium into the reactor, (C) a reactor discharge line configured to withdraw an effluent stream containing the oligomer product from the reactor, (D) an analytical system configured to determine an ethylene concentration in the reactor and/or in the reactor discharge line, the analytical system comprising an ultrasonic flow meter, and (E) a controller configured to control an ethylene flow rate of the ethylene into the reactor, a catalyst system flow rate of the catalyst system into the reactor, a reaction temperature, a reaction pressure, or any combination thereof, based on (or according to) the ethylene concentration determined by the analytical system.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description presented herein.

FIG. 4 presents a plot of a Raman ethylene peak versus speed of sound (m/sec) for Examples 4-8.

DEFINITIONS

Figure 1:
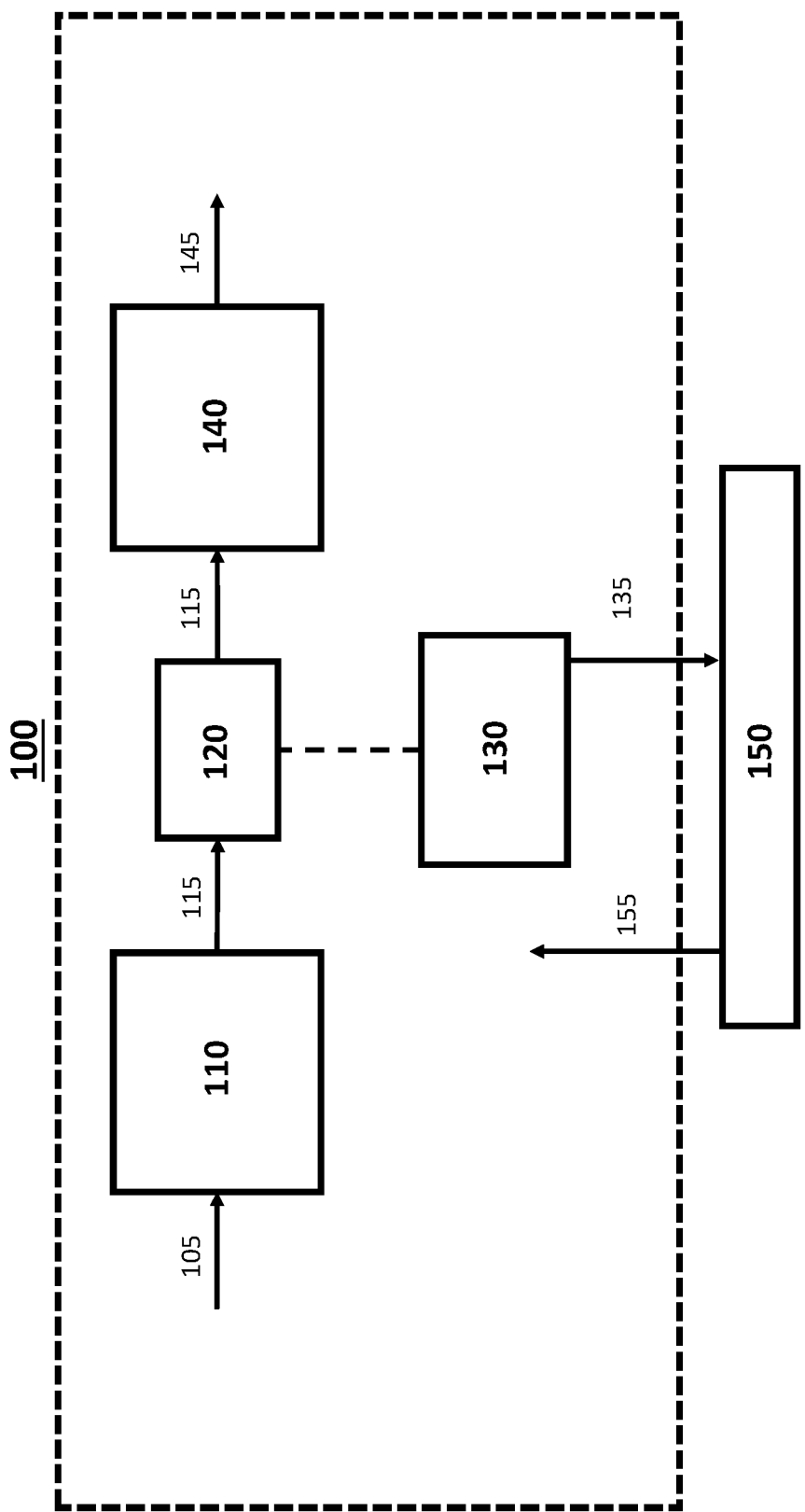
FIG. 1 illustrates a schematic diagram of an oligomerization reactor system consistent with an aspect of this invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and/or feature disclosed herein, all combinations that do not detrimentally affect the systems, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

In this disclosure, while compositions, processes/methods, and systems are described in terms of "comprising" various materials, steps, and components, the compositions, processes/methods, and systems also can "consist essentially of" or "consist of" the various materials, steps, or components, unless stated otherwise. The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

The terms "contacting" and "combining" are used herein to describe compositions, processes/methods, and systems in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the chromium compound/complex and the organoaluminum compound, after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon).

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane).

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used herein refers to any olefin that has a carbon-carbon double bond between the first and second carbon atom of the longest contiguous chain of carbon atoms. The term "alpha olefin" includes linear and branched alpha olefins and alpha olefins which can have more than one non-aromatic carbon-carbon double bond, unless expressly stated otherwise. The term "normal alpha olefin" as used herein refers to a linear aliphatic hydrocarbon mono-olefin having a carbon-carbon double bond between the first and second carbon atoms. The term "linear internal olefin" as used herein refers to a linear aliphatic hydrocarbon mono-olefin having a double bond that is not between the first and second carbon atoms.

The term oligomer refers to a compound that contains from 2 to 20 monomer units. The terms "oligomerization product" and "oligomer product" include all products made by the "oligomerization" process, including the "oligomers" and products which are not "oligomers" (e.g., products which contain more than 20 monomer units, or solid polymer), but exclude other non-oligomer components of an oligomerization reactor effluent stream, such as unreacted ethylene, organic reaction medium, and hydrogen, amongst other components.

The term "oligomerization" and its derivatives refer to processes which produce an oligomer product comprising at least 20 wt. %, 35 wt. %, 50 wt. %, or 60 wt. % products comprising from 2 to 20 monomer units. In an example, an "oligomerization" process using ethylene as the monomer produces a mixture of products comprising at least 20 wt. %, 35 wt. %, 50 wt. %, or 60 wt. % oligomers having from 4 to 40 carbon atoms, such as a total amount of $C_6$ olefins and $C_8$ olefins of least 50 wt. %, 65 wt. %, 75 wt. %, or 80 wt. %.

The term "effluent stream" generally refers to all the material which exits the reactor through a reactor outlet/discharge line, which discharges a reaction mixture and can include reaction zone feeds (e.g., ethylene, catalyst system or catalyst system components, and/or reaction medium), and reaction product (e.g., non-oligomers and an oligomer product containing oligomers).

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, there can be a range of linear velocities of the reaction mixture (or the effluent stream) through the ultrasonic flow meter in aspects of this invention. By a disclosure that the linear velocity is in a range from 0.5 to 20 ft/sec, the intent is to recite that the linear velocity can be any velocity in the range and, for example, can include any range or combination of ranges from 0.5 to 20 ft/sec, such as from 2 to 15 ft/sec, from 3 to 10 ft/sec, or from 3 to 8 ft/sec, and so forth. Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods, devices, and materials similar or equivalent to those described herein can be used in the practice or testing of the invention, the typical methods, devices, and materials are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

Methods for determining the ethylene concentration in an ethylene oligomerization reactor using an ultrasonic flow meter are disclosed, and these methods are integrated into related oligomerization processes and reactor systems. Herein, the speed of sound is measured in the ultrasonic flow meter, from which the ethylene concentration can be determined and monitored in real-time, and the oligomerization process and reactor system can be controlled based on the ethylene concentration. Beneficially, the response time to determine the speed of sound in the ultrasonic flow meter is very fast, and no probe or sampling is needed to determine the speed of sound data (or to determine the prevailing ethylene concentration in the stream flowing through the ultrasonic flow meter).

However, ethylene is but a very minor component of the stream flowing through the ultrasonic flow meter, whether the ultrasonic flow meter is positioned within the reactor or in the reactor discharge line. The reaction mixture (in the reactor) and the effluent stream (in the reactor discharge line) contain a complex mixture of materials, including ethylene, an organic reaction medium, hydrogen (if used), an oligomer product, and activated or deactivated catalyst system components. The oligomer product itself is a complex mixture of $C_4+$ hydrocarbons, and includes a variety of alkanes, $C_6$ olefins (e.g., 1-hexene), $C_8$ olefins (e.g., 1-octene), and $C_{10}+$ olefins.

In the reaction mixture or effluent stream flowing through the ultrasonic flow meter, the ethylene concentration may only range from 6 to 25 wt. % ethylene, although not necessarily limited thereto. The largest component of the reaction mixture or effluent stream flowing through the ultrasonic flow meter often is the organic reaction medium at 40 to 70 wt. %, with the oligomer product (and its vast array of components) often in the 15 to 30 wt. % range, although these amounts are not always limited to these particular ranges. Hydrogen and activated/deactivated catalyst system components also can be present in the reaction mixture or effluent stream flowing through the ultrasonic flow meter, but these are typically present in ppm levels (by weight).

It is apparent that a very complex mixture of materials in the reaction mixture or effluent stream flows the ultrasonic flow meter, and that of this complex mixture, only about 6-25% is ethylene. Therefore, one surprising result of this invention is the ability to determine the ethylene concentration (via a speed of sound measurement in an ultrasonic flow meter) of a complex mixture of a multitude of different components, and more surprisingly, when the component of interest (ethylene) is but a minor component in the overall mixture.

While not wishing to be bound by theory, it is believed that the methods described herein can successfully determine the ethylene concentration due to the large dependency of the speed of sound on density, and the density difference between ethylene and a majority of the other components in the reaction mixture or effluent stream is relatively large. Thus, small changes in ethylene concentration can be observed by comparing to an appropriate standard for the ethylene concentration, such as a calibration curve, or by using a mathematical model.

Oligomerization Reactor Systems

Various oligomerization reactor systems and processes for operating or controlling such systems are disclosed and described herein. For instance, a first process for operating an oligomerization reactor system can comprise (I) contacting ethylene, an organic reaction medium, optionally hydrogen, and a catalyst system comprising a heteroatomic ligand chromium compound complex and an organoaluminum compound, or a heteroatomic ligand, a chromium compound, and an organoaluminum compound, in a reactor within the oligomerization reactor system to form an oligomer product, (II) discharging an effluent stream containing the oligomer product from the reactor through a reactor discharge line, (III) determining an ethylene concentration in the reactor, and (IV) adjusting an ethylene flow rate of the ethylene into the reactor, a catalyst system flow rate of the catalyst system into the reactor, a reaction temperature, a reaction pressure, or any combination thereof, when the ethylene concentration has reached a predetermined level. The ethylene concentration in the reactor can be determined by (i) flowing a reaction mixture through an ultrasonic flow meter integrated into the reactor, (ii) determining a speed of sound in the reaction mixture from the ultrasonic flow meter, and (iii) correlating the speed of sound to a standard to determine the ethylene concentration in the reactor.

A second process for operating an oligomerization reactor system can comprise (I) contacting ethylene, an organic reaction medium, optionally hydrogen, and a catalyst system comprising a heteroatomic ligand chromium compound complex and an organoaluminum compound, or a heteroatomic ligand, a chromium compound, and an organoaluminum compound, in a reactor within the oligomerization reactor system to form an oligomer product, (II) discharging an effluent stream containing the oligomer product from the reactor through a reactor discharge line, (III) determining an ethylene concentration in the reactor discharge line, and (IV) adjusting an ethylene flow rate of the ethylene into the reactor, a catalyst system flow rate of the catalyst system into the reactor, a reaction temperature, a reaction pressure, or any combination thereof, when the ethylene concentration has reached a predetermined level. The ethylene concentration in the reactor discharge line can be determined by (i) flowing the effluent stream through an ultrasonic flow meter integrated into the reactor discharge line, (ii) determining a speed of sound in the effluent stream from the ultrasonic flow meter, and (iii) correlating the speed of sound to a standard to determine the ethylene concentration in the reactor discharge line.

Generally, the features of the first and second processes for operating oligomerization reactor systems disclosed herein (e.g., the feed components to the reactor, the oligomer product, the contents of the reactor (reaction mixture), the effluent stream, the ethylene concentration, the reactor, the method of determining the ethylene concentration, and the control of the ethylene concentration, among others) are independently described herein, and can be combined in any combination to further describe the disclosed processes. Moreover, other steps can be conducted before, during, and/or after any of the steps listed in the disclosed processes, unless stated otherwise.

Step (I) of the first process and the second process is directed to the production of an oligomer product. Ethylene, an organic reaction medium, optionally hydrogen, and a catalyst system (containing a heteroatomic ligand chromium compound complex and an organoaluminum compound, or a heteroatomic ligand, a chromium compound, and an organoaluminum compound) can be contacted in a reactor within the oligomerization reactor system to form the oligomer product. The ethylene oligomerization in step (I) can be performed in any manner known to a skilled artisan, using any suitable catalyst system, and any reactor(s) and reactor configuration. Representative ethylene oligomerization processes, reactor systems, and chromium-based catalyst compositions are disclosed in U.S. Patent Publication Nos. 2017/0081257, 2017/0341998, 2017/0341999, 2017/0342000, 2017/0342001, and 2016/0375431, and in U.S. Pat. Nos. 10,493,422, 10,464,862, 10,435,336, 10,689,312, and 10,807,921.

Generally, ethylene, the catalyst system or catalyst system components, the organic reaction medium, and hydrogen (if used) can be combined in any order or sequence and introduced into the reactor separately or in any combination. For instance, hydrogen and ethylene can be combined and fed to the reactor separately from the catalyst system or catalyst system components. This invention is not limited by the manner in which the respective components are introduced into the reactor.

Any suitable organic reaction medium can be used in the disclosed processes and reactor systems, such as a hydrocarbon reaction medium. Illustrative hydrocarbons can include, for example, aliphatic hydrocarbons, aromatic hydrocarbons, petroleum distillates, or combinations thereof; alternatively, aliphatic hydrocarbons; or alternatively, aromatic hydrocarbons. Aliphatic hydrocarbons which can be used as the organic reaction medium include $C_3$ to $C_{20}$ aliphatic hydrocarbons; alternatively, $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. In some aspects, the aliphatic hydrocarbon which can be utilized as the organic reaction medium can be a hydrocarbon olefin (linear or branched, or terminal or internal). Non-limiting examples of suitable acyclic aliphatic hydrocarbon reaction medium that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or a mixture of linear and branched $C_6$ acyclic aliphatic hydrocarbons); alternatively, heptane (n-heptane or a mixture of linear and branched $C_7$ acyclic aliphatic hydrocarbons); or alternatively, octane (n-octane or a mixture of linear and branched $C_8$ acyclic aliphatic hydrocarbons). In other aspects, the acyclic aliphatic reaction medium can be a product of the oligomerization (e.g., 1-hexene and/or 1-octene). Non-limiting examples of suitable cyclic aliphatic hydrocarbon reaction medium include cyclohexane and methyl cyclohexane; alternatively, cyclohexane; or alternatively, methylcyclohexane. Aromatic hydrocarbons which can be useful as an organic reaction medium include $C_6$ to $C_{20}$ aromatic hydrocarbons, or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof alternatively, benzene; alternatively, toluene; alternatively, xylene (including ortho-xylene, meta-xylene, para-xylene or mixtures thereof); or alternatively, ethylbenzene. In a particular aspect of this invention, the organic reaction medium can comprise, or consist essentially of, or consist of, cyclohexane.

The catalyst system or catalyst system components can comprise (i) a heteroatomic ligand chromium compound complex and an organoaluminum compound, or (ii) a heteroatomic ligand, a chromium compound, and an organoaluminum compound. This invention is not limited to any particular chromium-based oligomerization catalyst system, but typical heteroatomic ligand chromium compound complexes (and heteroatomic ligands and chromium compounds) and organoaluminum compound are disclosed in U.S. Patent Publication Nos. 2017/0081257, 2017/0341998, 2017/0341999, 2017/0342000, 2017/0342001, and 2016/0375431, and in U.S. Pat. Nos. 10,493,422, 10,464,862, 10,435,336, 10,689,312, and 10,807,921. Generally, the organoaluminum compound can be an aluminoxane, an alkylaluminum compound, or a combination thereof. Representative aluminoxanes include methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-entylaluminoxane, 3-pentyl-aluminoxane, iso-pentyl-aluminoxane, neopentylaluminoxane, and the like, while representative alkylaluminums include trimethylaluminum, tri ethyl aluminum, tripropylaluminum, tributylaluminum, trihexylaluminum, trioctylaluminum, and the like. Often, the Al to Cr molar ratio of the catalyst system can be in a range of 10:1 to 5,000:1, from 50:1 to 3,000:1, from 50:1 to 3,000:1, from 75:1 to 2,000:1, from 100:1 to 2,000:1, of from 100:1 to 1,000:1. If more than one chromium complex and/or more than one organoaluminum are employed, the Al to Cr ratio is based on the total moles of chromium and/or aluminum.

Forming the oligomer product in the reactor can be accomplished at any suitable oligomerization temperature and pressure. Often, the oligomer product can be formed at a minimum temperature of 0° C., 20° C., 40° C., 60° C., 70° C., or 75° C.; additionally or alternatively, at a maximum temperature of 160° C., 150° C., 140° C., 130° C., 115° C., 100° C., or 95° C. Generally, the oligomerization temperature at which the oligomer product is formed can be in a range from any minimum temperature disclosed herein to any maximum temperature disclosed herein. Accordingly, suitable non-limiting ranges can include the following: from 0 to 160° C., from 20 to 160° C., from 40 to 160° C., from 40 to 150° C., from 40 to 100° C., from 60 to 130° C., from 60 to 115° C., from 60 to 100° C., from 70 to 115° C., from 70 to 100° C., or from 75 to 95° C. Other appropriate oligomerization temperatures and temperature ranges are readily apparent from this disclosure.

The oligomer product can be formed at a minimum pressure (or ethylene partial pressure) of 50 psig, 100 psig, 200 psig, 400 psig, 600 psig, or 700 psig; additionally or alternatively, at a maximum pressure (or ethylene partial pressure) of 3000 psig, 2000 psig, 1500 psig, 1300 psig, or 1200 psig. Generally, the oligomerization pressure (or ethylene partial pressure) at which the oligomer product is formed can be in a range from any minimum pressure disclosed herein to any maximum pressure disclosed herein. Accordingly, suitable non-limiting ranges can include the following: from 50 psig to 3000 psig, from 100 psig to 200 psig, from 200 psig to 2000 psig, from 200 psig to 1200 psig, from 400 psig to 1500 psig, from 400 psig to 1200 psig, from 600 psig to 2000 psig, from 600 psig to 1300 psig, from 700 psig to 1500 psig, or from 700 psig to 1200 psig. Other appropriate oligomerization pressures (or ethylene partial pressures) are readily apparent from this disclosure.

When used, hydrogen can be fed directly to the reactor, or hydrogen can be combined with an ethylene feed prior to the reactor. In the reactor, the hydrogen partial pressure can be at least 1 psig (6.9 kPa), 5 psig (34 kPa), 10 psig (69 kPa), 25 psig (172 kPa), or 50 psig (345 kPa); additionally or alternatively, a maximum hydrogen partial pressure of 2000 psig (13.8 MPa), 1750 psig (12.1 MPa), 1500 psig (10.3 MPa), 1250 psig (8.6 MPa), 1000 psig (6.9 MPa), 750 psig (5.2 MPa), 500 psig (3.4 MPa), or 400 psig (2.8 MPa). Generally, the hydrogen partial pressure can range from any minimum hydrogen partial pressure disclosed herein to any maximum hydrogen partial pressure disclosed herein. Therefore, suitable non-limiting ranges for the hydrogen partial pressure can include the following ranges: from 1 psig (6.9 kPa) to 2000 psig (13.8 MPa), from 1 psig (6.9 kPa) to 1750 psig (12.1 MPa), from 5 psig (34 kPa) to 1500 psig (10.3 MPa), from 5 psig (34 kPa) to 1250 psig (8.6 MPa), from 10 psig (69 kPa) to 1000 psig (6.9 MPa), from 10 psig (69 kPa) to 750 psig (5.2 MPa), from 10 psig (69 kPa) to 500 psig (3.5 MPa), from 25 psig (172 kPa) to 750 psig (5.2 MPa), from 25 psig (172 kPa) to 500 psig (3.4 MPa), from 25 psig (172 kPa) to 400 psig (2.8 MPa), or from 50 psig (345 kPa) to 500 psig (3.4 MPa). Other appropriate hydrogen partial pressures in the reactor for the formation of the oligomer product are readily apparent from this disclosure.

The ethylene conversion in the first process and the second process is not particularly limited, but often ranges from 40 to 80%. Typical minimum ethylene conversions include 40%, 45%, and 50%, and typical maximum ethylene conversions include 80%, 75%, and 70%. Generally, the ethylene conversion can range from any minimum conversion disclosed herein to any maximum conversion disclosed herein. Therefore, suitable non-limiting ranges for the ethylene conversion include from 40 to 80%, from 40 to 75%, or from 45 to 80%, 45 to 75%, from 50 to 80%, or from 50 to 70%. Ethylene conversion is based on the amount of ethylene entering the reactor system (moles) and the amount of ethylene in the effluent stream in the reactor discharge line (moles). Other appropriate ethylene conversions in the oligomerization processes and reactor systems are readily apparent from this disclosure.

The oligomerization reactor in which the oligomer product is formed can comprise any suitable reactor. Non-limiting examples of reactor types can include a stirred tank reactor, a plug flow reactor, or any combination thereof alternatively, a fixed bed reactor, a continuous stirred tank reactor, a loop reactor, a solution reactor, a tubular reactor, a recycle reactor, or any combination thereof. In an aspect, the oligomerization reactor system can have more than one reactor in series and/or in parallel, and including any combination of reactor types and arrangements. Moreover, the oligomerization process used to form the oligomer product can be a continuous process or a batch process, or any reactor or reactors within the oligomerization reaction system can be operated continuously or batchwise.

The oligomer product can contain $C_4+$ hydrocarbons and generally the vast majority of the oligomer product is $C_6$ olefins and/or $C_8$ olefins. In an aspect, the minimum amount (total) of $C_6$ olefins and $C_8$ olefins can be 50 wt. %, 65 wt. %, 75 wt. %, 80 wt. %, 82 wt. %, or 85 wt. %. In another aspect, the maximum amount (total) of $C_6$ olefins and $C_8$ olefins in the oligomer product can be 99 wt. %, 95 wt. %, 92.5 wt. %, or 90 wt. %. Generally, the total amount of $C_6$ olefins and $C_8$ olefins in the oligomer product can range from any minimum amount to any maximum amount of described herein. For instance, the total amount of $C_6$ olefins and $C_8$ olefins—based on the total weight of oligomers in the oligomer product—can be from 50 wt. % to 99 wt. %, from 65 wt. % to 95 wt. %, from 65 wt. % to 90 wt. %, from 75 wt. % to 95 wt. %, from 80 wt. % to 99 wt. %, from 80 wt. % to 92.5 wt. %, from 82 wt. % to 99 wt. %, from 82 wt. % to 90 wt. %, from 85 wt. % to 99 wt. %, or from 85 wt. % to 95 wt. %. Other appropriate total amounts of $C_6$ olefins and $C_8$ olefins in the oligomer product are readily apparent from this disclosure.

In step (II), an effluent stream containing the oligomer product is discharged from the reactor through a reactor discharge line. As disclosed herein, the effluent stream generally refers to all the material which exits the reactor through a reactor discharge line. The effluent stream can include feed materials to the reactor that have not been completely reacted or consumed (e.g., ethylene, catalyst system or catalyst system components, and/or organic reaction medium), the oligomer products (e.g., $C_6$ olefins and $C_8$ olefins, and higher ethylene oligomers), and non-oligomer reaction products (e.g., alkanes).

In a similar manner, the reaction mixture refers to the contents in the reactor, prior to discharge. Thus, like the effluent stream, the reaction mixture can include feed materials to the reactor that have not been completely reacted or consumed (e.g., ethylene, catalyst system or catalyst system components, and/or organic reaction medium), the oligomer products (e.g., $C_6$ olefins and $C_8$ olefins, and higher ethylene oligomers), and non-oligomer reaction products (e.g., alkanes).

In some aspects of this invention, the compositional breakdown of the reaction mixture and the effluent stream is the same, while in other aspects, the compositional breakdown of the reaction mixture and the effluent stream is different. This can depend, for instance, on the type of reactor(s) in the oligomerization reactor system, such as a continuous stirred tank reactor, a loop reactor, and so forth.

Regardless of the reactor type(s) and the exact composition, it is apparent that the reaction mixture and the effluent stream both contain a complex mixture of a multitude of different materials, including ethylene, organic reaction medium, hydrogen (if used), the oligomer product, and activated or deactivated catalyst system components. While not limited thereto, the reaction mixture and the effluent stream can contain ethylene in an amount, independently, from 6 to 25 wt. %, from 10 to 25 wt. %, from 11 to 22 wt. %, from 12 to 20 wt. %, or from 13 to 18 wt. %. Additionally or alternatively, the amount of the organic reaction medium in the reaction mixture and the effluent stream, independently, can range from 40 to 70 wt. %, such as from 40 to 65 wt. %, or from 45 to 65 wt. %. Additionally or alternatively, the reaction mixture and the effluent stream, independently, can contain from 15 to 30 wt. %, from 16 to 28 wt. %, from 17 to 27 wt. %, or from 17 to 24 wt. %, of the oligomer product.

Hydrogen and catalyst system components, when present in the reaction mixture and/or the effluent stream, are in relatively minor amounts. For instance, the reaction mixture and the effluent stream can contain an amount of hydrogen, independently, in a range from greater than 0 to 250 ppm, from greater than 0 to 100 ppm, or from 10 to 75 ppm, of hydrogen. These ppm amounts by weight are based on the total weight of the respective reaction mixture or effluent stream.

The total amount of catalyst system components—whether activated or deactivated—in the reaction mixture and the effluent stream, independently, often can range from 10 to 1000 ppm, from 20 to 500 ppm, or from 20 to 250 ppm, although not limited thereto. As above, these ppm amounts by weight are based on the total weight of the respective reaction mixture or effluent stream.

In step (III) of the first process, the ethylene concentration in the reactor is determined by, or via the steps of, (i) flowing a reaction mixture through an ultrasonic flow meter integrated into the reactor, (ii) determining a speed of sound in the reaction mixture from the ultrasonic flow meter, and (iii) correlating the speed of sound to a standard to determine the ethylene concentration in the reactor, while in step (III) of the second process, the ethylene concentration in the reactor discharge line is determined by, or via the steps of (i) flowing the effluent stream through an ultrasonic flow meter integrated into the reactor discharge line, (ii) determining a speed of sound in the effluent stream from the ultrasonic flow meter, and (iii) correlating the speed of sound to a standard to determine the ethylene concentration in the reactor discharge line.

Referring first to step (i) of the first process, the reaction mixture is flowed through the ultrasonic flow meter integrated into the reactor. The ultrasonic flow meter can be integrated into the reactor in any suitable manner such that the oligomerization process is not detrimentally impacted and a representative distribution of the reactor contents (the reaction mixture) is flowed through the ultrasonic flow meter. As an example, the ultrasonic flow meter can comprise a length of pipe integrated into the reactor. Suitably, the length of pipe can have the same inside diameter (ID) as that of the reactor. For a loop reactor, the length of pipe can have the same ID as the loop reactor, and the reaction mixture flows through the ultrasonic flow meter typically on a continuous basis.

As to step (i) of the second process, the effluent stream is flowed through the ultrasonic flow meter integrated into the reactor discharge line. The ultrasonic flow meter can be integrated into the reactor discharge line in any suitable manner such that the oligomerization process is not detrimentally impacted and a representative distribution of the effluent stream is flowed through the ultrasonic flow meter. As an example, the ultrasonic flow meter can comprise a length of pipe integrated into the reactor discharge line, and often prior to any pressure relief. Suitably, the length of pipe can have the same inside diameter (ID) as that of the reactor discharge line. For a continuous stirred tank reactor, the length of pipe can have the same ID as the discharge line from the reactor, and the effluent stream flows through the ultrasonic flow meter typically on a continuous basis.

Regardless of whether the reaction mixture is flowing through the ultrasonic flow meter integrated into the reactor or whether the effluent stream is flowing through the ultrasonic flow meter integrated into the reactor discharge line, any suitable linear velocity of the reaction mixture or the effluent stream through the ultrasonic flow meter can be utilized. This linear flow rate can depend, for instance, upon the type of reactor and the composition of the reaction mixture (or effluent stream), among other factors. Generally, however, the linear velocity falls within a range from 0.5 to 20 ft/sec or from 2 to 15 ft/sec in some aspects, and from 3 to 10 ft/sec or from 3 to 8 ft/sec, in other aspects.

In step (ii), the speed of sound in the reaction mixture (or in the effluent stream) is determined from the ultrasonic flow meter. By flowing the reaction mixture through the ultrasonic flow meter integrated into the reactor at an appropriate linear velocity, or by flowing the effluent stream through the ultrasonic flow meter integrated into the reactor discharge line at an appropriate linear velocity, the ultrasonic flow meter determines the respective speed of sound data.

In step (iii), the speed of sound is correlated to a standard to determine the ethylene concentration in the reactor (or in the reactor discharge line). In an aspect, the standard can comprise a calibration curve. The step of correlating can be performed manually or can be performed automatically. If calibration curves are used, these calibration curves can be generated by any procedure known to one of skill in the art, non-limiting illustrations of which are shown in the examples that follow. Thus, the step of correlating the speed of sound can comprise any suitable method that converts the speed of sound into the ethylene concentration.

The step of correlating can comprise any suitable method or technique that converts the speed of sound into the ethylene concentration. The correlation step can be performed manually, or can be configured to automatically convert speed of sound data—e.g., via a mathematical model—into the ethylene concentration.

In some instances, actual speed of sound numbers can be generated, which can be collected or outputted, viewed on a monitor or computer screen, or printed in hard copy form. In other instances, the speed of sound values are generated, but not collected or outputted into a viewable form. For example, speed of sound data from the ultrasonic flow meter can be directly converted (or automatically converted) into the ethylene concentration in the reactor (or in the reactor discharge line) by correlating to a standard, such as a calibration curve or mathematical model.

In step (IV) of the first process and the second process, the ethylene flow rate of the ethylene into the reactor, the catalyst system flow rate of the catalyst system into the reactor, the reaction temperature, the reaction pressure, or any combination thereof, is/are adjusted when the ethylene concentration has reached a predetermined level. Or, in alternative language, the ethylene flow rate, the catalyst system flow rate, the reaction temperature, the reaction pressure, or any combination thereof, is/are adjusted based on the determined ethylene concentration. Hence, the feed rates of ethylene and/or the catalyst into the reactor and/or process conditions (e.g., reaction temperature, reaction pressure) can be adjusted, manually and/or automatically, based on the determined concentration of ethylene in the reactor (or in the reactor discharge line). Any units for concentration of ethylene can be used, but often, wt. % in the reaction mixture or in the effluent stream is used.

The processes disclosed herein are applicable to a wide variety of circumstances where the ethylene concentration during an oligomerization process may be of interest. For instance, when the ethylene concentration has reached a predetermined level, the ethylene flow rate of ethylene into the reactor can be adjusted. The predetermined level can be readily ascertained by one of skill in the art depending upon, for instance, the historic and the prevailing conditions in the oligomerization reactor system. As a non-limiting example, a predetermined level can be a decrease of a certain percentage of the ethylene concentration (e.g., beyond that which is deemed allowable during normal on-prime production). For instance, the target ethylene concentration for a particular ethylene oligomerization process can be 15 wt. %, based on the reaction mixture (or based on the effluent stream), and the predetermined lower and upper control limits can be 13 wt. % and 17 wt. %, respectively, for normal on-prime production. If the measured ethylene concentration was in the 10-12 wt. % range, then the ethylene feed rate of the ethylene into the oligomerization reactor can be increased to increase the concentration of ethylene in the reactor (or in the effluent stream), such that the ethylene concentration in the reactor (or in the effluent stream) is increased due to the increased addition amount of the ethylene.

As the example above demonstrates, in one aspect, the ethylene flow rate can be adjusted in step (IV). In another aspect, the catalyst system flow rate can be adjusted in step (IV). In another aspect, the reaction temperature can be adjusted in step (IV). In yet another aspect, the reaction pressure can be adjusted in step (IV). In still another aspect, two or more of the ethylene flow rate, the catalyst system flow rate, the reaction temperature, and the reaction pressure can be adjusted in step (IV).

In another aspect of this invention, an oligomerization reactor system is provided, and in this aspect, the oligomerization reactor system can comprise (A) a reactor configured to contact a catalyst system with ethylene, an organic reaction medium, and optional hydrogen under oligomerization conditions to produce an oligomer product, (B) one or more reactor inlets configured to introduce the catalyst system, ethylene, and the organic reaction medium into the reactor, (C) a reactor discharge line configured to withdraw an effluent stream containing the oligomer product from the reactor, (D) an analytical system configured to determine an ethylene concentration in the reactor and/or in the reactor discharge line, the analytical system comprising an ultrasonic flow meter, and (E) a controller configured to control an ethylene flow rate of the ethylene into the reactor, a catalyst system flow rate of the catalyst system into the reactor, a reaction temperature, a reaction pressure, or any combination thereof, based on (or according to) the ethylene concentration determined by the analytical system. Generally, the features of any of the oligomerization reactor systems disclosed herein (e.g., the reactor, the catalyst system, the reactor inlets, the analytical system, and the controller, among others) are independently described herein, and these features can be combined in any combination to further describe the disclosed oligomerization reactor systems. Moreover, other devices or reactor system components in addition to the reactor, the reactor inlets, the reactor discharge line, the analytical system, and the controller, can be present in the disclosed oligomerization reactor systems, unless stated otherwise.

The (A) reactor is configured to contact a catalyst system with ethylene, an organic reaction medium, and optional hydrogen under oligomerization conditions to produce an oligomer product. Thus, any suitable oligomerization reactor can be utilized in the reactor system. As described herein, non-limiting examples of reactor types can include a stirred tank reactor, a plug flow reactor, or any combination thereof; alternatively, a fixed bed reactor, a continuous stirred tank reactor, a loop reactor, a solution reactor, a tubular reactor, a recycle reactor, or any combination thereof; or alternatively, a loop reactor. The oligomerization reactor system can have more than one reactor in series and/or in parallel, and including any combination of reactor types and arrangements, and moreover, any reactor or reactors within the oligomerization reaction system can be operated continuously or batchwise.

The (B) one or more reactor inlets are configured to introduce the catalyst system, ethylene, and the organic reaction medium into the reactor. This invention is not limited by the number of reactor inlets that are used to introduce the respective components into the reactor. For instance, each component can be fed to the reactor separately, with its own reactor inlet, in one aspect, while in another aspect, two or more components can be combined and the resulting mixture can be fed to the reactor via a reactor inlet. In addition, the one or more reactor inlets can be further configured to introduce hydrogen into the reactor. A separate reactor inlet for hydrogen can be used, or hydrogen can combined with another component—such as ethylene—and the resulting mixture can be fed to the reactor via a reactor inlet.

The catalyst system can comprise a heteroatomic ligand chromium compound complex and an organoaluminum compound, or a heteroatomic ligand, a chromium compound, and an organoaluminum compound. As above, components of the catalyst system can be fed separately to the reactor with their own reactor inlet, or the already formed catalyst system can be fed directly to the reactor via a reactor inlet.

The oligomerization reactor system includes the (C) reactor discharge line, which is configured to withdraw an effluent stream containing the oligomer product from the reactor. The oligomerization reactor system also includes the (D) analytical system, which is designed to determine the ethylene concentration in the reactor (or in the reactor discharge line, or both), and the analytical system comprises an ultrasonic flow meter. As described herein, the ultrasonic flow meter can be integrated into the reactor, and the ultrasonic flow meter can comprise, for instance, a length of pipe integrated into the reactor, and moreover, the ultrasonic flow meter can have the same ID as the reactor. This arrangement can be used for a loop reactor, among other reactor types.

Additionally or alternatively, the ultrasonic flow meter can be integrated into the reactor discharge line. Hence, the ultrasonic flow meter can comprise a length of pipe integrated into the reactor discharge line, and moreover, the ultrasonic flow meter can have the same ID as the reactor discharge line. This arrangement can be used for a stirred tank reactor or a loop reactor, among other reactor types.

The ultrasonic flow meter generally is designed to determine the speed of sound in the reactor mixture in the reactor (or in the effluent stream in the reactor discharge line). In addition to the ultrasonic flow meter, the analytical system can include any suitable component for correlating the speed of sound to a standard to determine the ethylene concentration in the reactor (or in the reactor discharge line). This can be accomplished manually using a standard such as a calibration curve, or a mathematical model. The analytical system also can include a computer or other related apparatus that takes the speed of sound output from the ultrasonic flow meter and automatically converts that output into the ethylene concentration. The step of correlating can comprise any suitable technique for converting the speed of sound output into the ethylene concentration; one such suitable technique is a mathematical model correlating the speed of sound and the ethylene concentration.

The oligomerization reactor system can further include the (E) controller that is configured to control an ethylene flow rate of the ethylene into the reactor, a catalyst system flow rate of the catalyst system into the reactor, a reaction temperature, a reaction pressure, or any combination thereof, based on—or according to—the ethylene concentration determined by the analytical system.

The controller, which can comprise any suitable processing unit or computer system, can be used to analyze the data regarding the ethylene concentration, and adjust one or more of the ethylene flow rate, the catalyst system flow rate, the reaction temperature, and/or the reaction pressure, based on the determined ethylene concentration. In another aspect, the controller can be programmed with an algorithm to control one or more of the ethylene flow rate, the catalyst system flow rate, the reaction temperature, and/or the reaction pressure, based on the ethylene concentration determined by the analytical system. As an example, if the ethylene concentration determined by the analytical system is too low, the ethylene flow rate into the reactor can be increased by the controller.

The controller can be operated on an as-needed basis, at set time intervals, or continuously, depending upon the requirements of the reactor system. Thus, it is contemplated that the ethylene concentration in the reactor and/or in the reactor discharge line can be monitored and/or adjusted and/or controlled continuously. Accordingly, in particular aspects consistent with this invention, the oligomerization reactor system and the controller can operate in real-time or near real-time, such that the ethylene concentration can be determined, and that determined ethylene concentration can be used, instantaneously or nearly instantaneously, to adjust one or more of the ethylene flow rate, the catalyst system flow rate, the reaction temperature, and/or the reaction pressure, The controller or computing device can be implemented using a personal computer, a network computer, a server, a mainframe, or other similar microcomputer-based workstation. The controller or computing device can comprise any computer operating environment, such as hand-held devices, multiprocessor systems, microprocessor-based or programmable sender electronic devices, minicomputers, mainframe computers, and the like. The controller or computing device also can be practiced in distributed computing environments where tasks are performed by remote processing devices. Furthermore, the controller or computing device can comprise a mobile terminal, such as a smart phone, a cellular telephone, a cellular telephone utilizing wireless application protocol (WAP), personal digital assistant (PDA), intelligent pager, portable computer, a hand held computer, a conventional telephone, a wireless fidelity (Wi-Fi) access point, or a facsimile machine. The aforementioned systems and devices are examples, and the controller or computing device can comprise other systems or devices. Controller or computing device also can be implemented via a system-on-a-chip (SOC) where each and/or many of the components illustrated above can be integrated onto a single integrated circuit. Such an SOC device can include one or more processing units, graphics units, communications units, system virtualization units and various application functionalities, all of which can be integrated (or "burned") onto the chip substrate as a single integrated circuit. Other controller methodologies and devices are readily apparent to one of skill in the art in view of this disclosure.

Controllers of the systems disclosed herein can control one or more of the ethylene flow rate, the catalyst system flow rate, the reaction temperature, and/or the reaction pressure, in the oligomerization reactor system by any method that affords precise and near instantaneous control based on the ethylene concentration determined by the analytical system.

A representative oligomerization reactor system 100 consistent with aspects of this invention, and related to the second process for operating an oligomerization reactor system is illustrated in FIG. 1. The oligomerization reactor system 100 includes a reactor 110, an ultrasonic flow meter 120, an analytical system 130, a fractionation system 140, and a controller 150. The reactor 110 is any reactor suitable for contacting a catalyst system with ethylene, an organic reaction medium, and optionally hydrogen under oligomerization conditions to produce an oligomer product. The oligomerization reactor system 100 includes a reactor inlet 105, which introduces the catalyst system, ethylene, and the organic reaction medium (and hydrogen, if used) into the reactor 110. Only one reactor inlet is shown in FIG. 1, but the presence of more than one reactor inlet for separate introduction of the various feed components is encompassed herein, as such would be recognized by those of skill in the art.

The oligomerization reactor system 110 includes a reactor discharge line 115, where the effluent stream containing the oligomer product is discharged from the reactor. In FIG. 1, the ultrasonic flow meter 120 is incorporated into the reactor discharge line 115. While not a requirement for the oligomerization reactor system 100, FIG. 1 illustrates the fractionation system 140, which can take the reactor effluent (and oligomer product) from the reactor discharge line 115 and separate the oligomer product into one or more product fraction streams 145, such as a $C_6$ olefin product stream (e.g., containing predominantly 1-hexene), a $C_8$ olefin product stream (e.g., containing predominantly 1-octene), and so forth.

The analytical system 130 in FIG. 1 is designed to determine the ethylene concentration in the reactor discharge line 115, and the analytical system includes and is in communication with the ultrasonic flow meter 120, which measures the speed of sound in the effluent stream in the reactor discharge line 115.

Information or data 135 on the ethylene concentration in the reactor discharge line 115 determined by the analytical system 130 can be provided to controller 150, which can then control or adjust 155 an ethylene flow rate of the ethylene via reactor inlet 105 into the reactor 110, a catalyst system flow rate of the catalyst system via reactor inlet 105 into the reactor 110, a reaction temperature in the reactor 110, a reaction pressure in the reactor 110, or any combination thereof, based on (or according to) the ethylene concentration determined by the analytical system 130. For example, if the ethylene concentration in the reactor discharge line 115 determined by the analytical system 130 is too low or below a target value, the controller 150 can increase the ethylene flow rate of the ethylene via reactor inlet 105 into the reactor 110.

Figure 2:
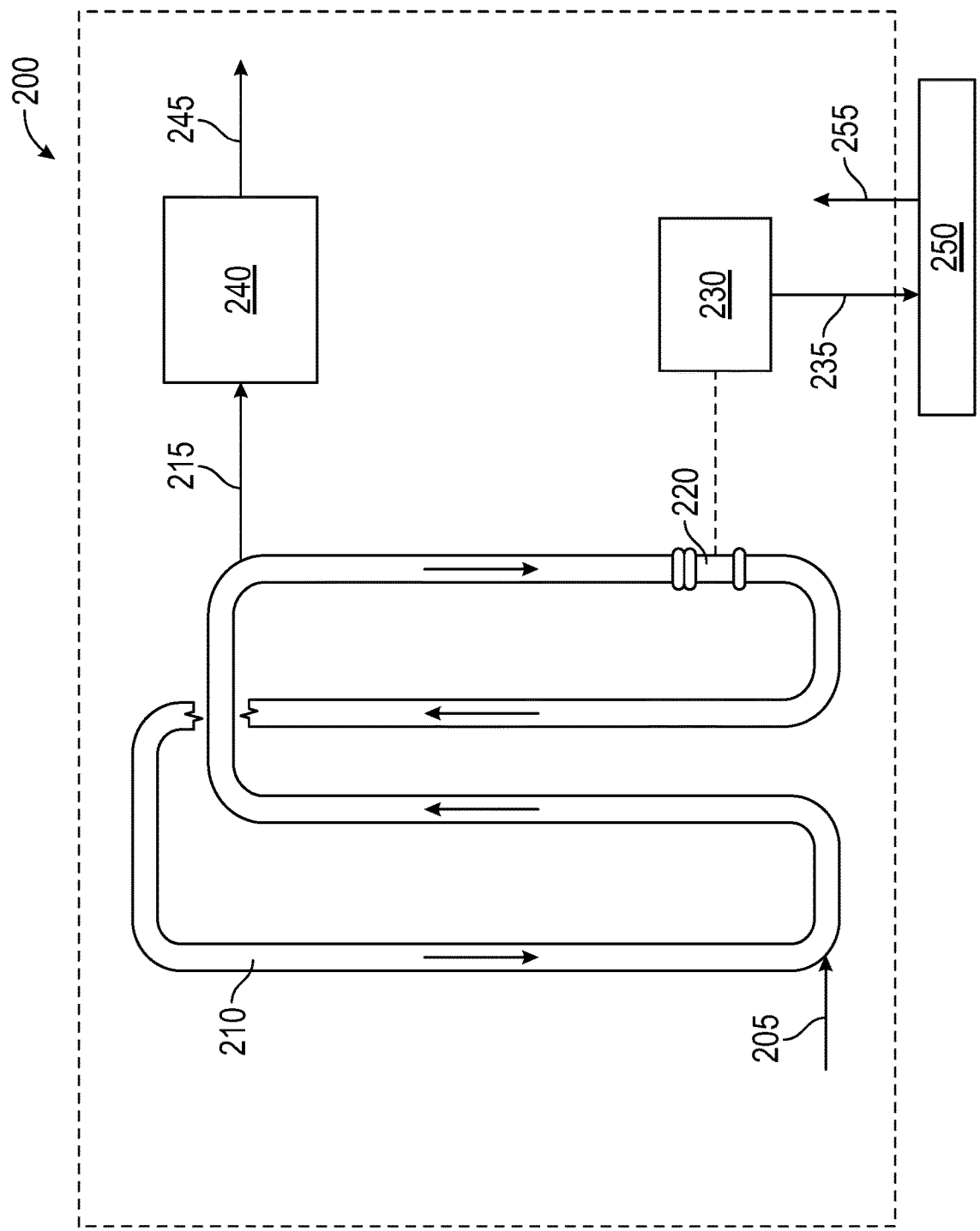
FIG. 2 illustrates a schematic diagram of an oligomerization reactor system consistent with another aspect of this invention.

Referring now to FIG. 2, which illustrates another ethylene oligomerization reactor system 200 consistent with another aspect of the present invention. The oligomerization reactor system 200 includes a reactor inlet 205 (one or more), a reactor 210, a reactor discharge line 215 (one or more), an analytical system 230, information or data 235 on the ethylene concentration, a fractionation system 240, a product stream 245 (one or more), and a controller 250 which can control or adjust 255 process variables, and these are generally the same as described above for the similarly numbered components in FIG. 1.

However, FIG. 2 illustrates the ultrasonic flow meter 220 incorporated into the reactor 210, shown representatively as a loop reactor. The analytical system 230 in FIG. 2 is designed to determine the ethylene concentration in the reactor 210, and the analytical system includes and is in communication with the ultrasonic flow meter 220, which is integrated as part of the reactor 210 and measures the speed of sound in the reaction mixture (reactor contents) flowing within the reactor 210.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Pilot plant ethylene oligomerization experiments were conducted in a loop reactor in which a segment was replaced with a Krohne Optisonic 3400 ultrasonic flow meter having a 2-inch ID. For the experiments, the linear velocity through the loop and flow meter was in the 3-6 ft/sec range, the reaction temperature was in the 60-100° C. range, the reaction pressure was in the 700-1000 psig range, and the organic reaction medium was cyclohexane. The catalyst system included a $N^2$-phosphinyl guanidine chromium(III) trichloride tetrahydrofuran complex and MAO at an Al:Cr molar ratio of 200:1-1000:1. A small amount of hydrogen also was charged into the reactor.

Figure 3:
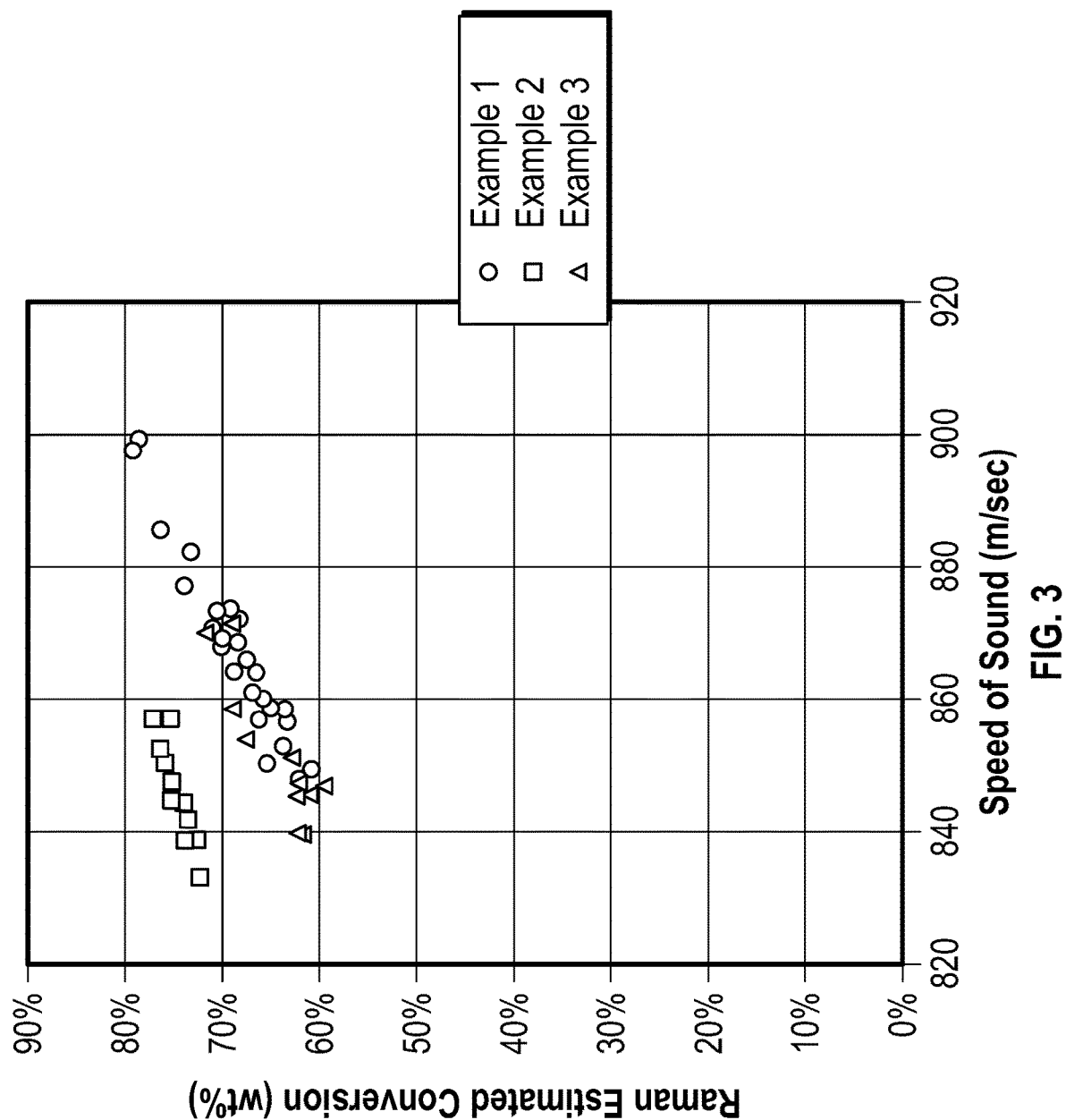
FIG. 3 presents a plot of Raman ethylene conversion (wt. %) versus speed of sound (m/sec) for Examples 1-3.

FIG. 3 summarizes Examples 1-3. For Examples 1 and 3, the ethylene feed rate was 25 lb/hr and the cyclohexane feed rate was 60 lb/hr. For 60 wt. %, 70 wt. %, and 80 wt. % conversion, the approximate ethylene concentrations based on Raman spectroscopy were 12 wt. %, 9 wt. %, and 6 wt. %, respectively. Importantly, even at these low ethylene concentrations—and, therefore, large amounts of reaction medium and oligomer products—the correlation, unexpectedly, between ethylene conversion (or ethylene concentration) and the speed of sound in the reaction mixtures for Examples 1 and 3 in FIG. 3 was excellent.

For Example 2, the ethylene feed rate was 30 lb/hr and the cyclohexane feed rate was 60 lb/hr. For 70 wt. % and 75 wt. % conversion, the approximate ethylene concentrations based on Raman spectroscopy were 10 wt. % and 8 wt. %, respectively. Similar to Examples 1 and 3, the correlation between ethylene conversion (or ethylene concentration) and the speed of sound in the reaction mixtures for Example 2 in FIG. 3 also was surprisingly good.

FIG. 4 summarizes Examples 4-8, which were performed similarly to that of Examples 1-3, and which cover a range of Raman ethylene peak amounts (which are directly related to ethylene concentration) and speeds of sound ranging from 800 to 1000 m/sec. The baseline is for a mixture of ethylene and cyclohexane (no oligomer product, catalyst, etc.); when no ethylene is present, the speed of sound in cyclohexane was approximately 1012 m/sec. Examples 4-8 cover of range of Raman ethylene peaks from 0 to 2.5 (which converts to a range of ethylene concentrations from 0 to 35 wt. % ethylene). Unexpectedly, given the presence of large amounts of cyclohexane and oligomer product, the correlation with speed of sound over this wide range of ethylene concentration was excellent.

Collectively, FIGS. 3-4 demonstrate that with appropriate standards (e.g., calibration charts, mathematical models), the ethylene concentration in a complex mixture of numerous other components can be readily correlated to speed of sound data, and that the ethylene concentration can be monitored and adjusted in real-time.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of" unless specifically stated otherwise):

Aspect 1. A process for operating an oligomerization reactor system, the process comprising:

(I) contacting ethylene, an organic reaction medium, optionally hydrogen, and a catalyst system comprising a heteroatomic ligand chromium compound complex and an organoaluminum compound, or a heteroatomic ligand, a chromium compound, and an organoaluminum compound, in a reactor within the oligomerization reactor system to form an oligomer product;

(II) discharging an effluent stream containing the oligomer product from the reactor through a reactor discharge line;

(III) determining an ethylene concentration in the reactor by (or via the steps of): (i) flowing a reaction mixture through an ultrasonic flow meter integrated into the reactor; (ii) determining a speed of sound in the reaction mixture from the ultrasonic flow meter; and (iii) correlating the speed of sound to a standard to determine the ethylene concentration in the reactor; and (IV) adjusting an ethylene flow rate of the ethylene into the reactor, a catalyst system flow rate of the catalyst system into the reactor, a reaction temperature, a reaction pressure, or any combination thereof, when the ethylene concentration has reached a predetermined level (or adjusting the ethylene flow rate, the catalyst system flow rate, the reaction temperature, the reaction pressure, or any combination thereof, based on the determined ethylene concentration).

Aspect 2. A process for operating an oligomerization reactor system, the process comprising:

(I) contacting ethylene, an organic reaction medium, optionally hydrogen, and a catalyst system comprising a heteroatomic ligand chromium compound complex and an organoaluminum compound, or a heteroatomic ligand, a chromium compound, and an organoaluminum compound, in a reactor within the oligomerization reactor system to form an oligomer product;

(II) discharging an effluent stream containing the oligomer product from the reactor through a reactor discharge line;

(III) determining an ethylene concentration in the reactor discharge line by (or via the steps of): (i) flowing the effluent stream through an ultrasonic flow meter integrated into the reactor discharge line; (ii) determining a speed of sound in the effluent stream from the ultrasonic flow meter; and (iii) correlating the speed of sound to a standard to determine the ethylene concentration in the reactor discharge line; and (IV) adjusting an ethylene flow rate of the ethylene into the reactor, a catalyst system flow rate of the catalyst system into the reactor, a reaction temperature, a reaction pressure, or any combination thereof, when the ethylene concentration has reached a predetermined level (or adjusting the ethylene flow rate, the catalyst system flow rate, the reaction temperature, the reaction pressure, or any combination thereof, based on the determined ethylene concentration).

Aspect 3. The process defined in aspect 1 or 2, wherein the reaction mixture (or the effluent stream) comprises ethylene, the organic reaction medium, optionally hydrogen, the oligomer product, and activated or deactivated catalyst system components.

Aspect 4. The process defined in any one of the preceding aspects, wherein the reaction mixture (or the effluent stream) comprises any suitable ethylene concentration, e.g., from 6 to 25 wt. %, from 10 to 25 wt. %, from 11 to 22 wt. %, from 12 to 20 wt. %, or from 13 to 18 wt. %.

Aspect 5. The process defined in any one of the preceding aspects, wherein the reaction mixture (or the effluent stream) comprises any suitable amount of the organic reaction medium, e.g., from 40 to 70 wt. %, from 40 to 65 wt. %, or from 45 to 65 wt. %.

Aspect 6. The process defined in any one of the preceding aspects, wherein the reaction mixture (or the effluent stream) comprises any suitable amount of the oligomer product, e.g., from 15 to 30 wt. %, from 16 to 28 wt. %, from 17 to 27 wt. %, or from 17 to 24 wt. %.

Aspect 7. The process defined in aspect 6, wherein the oligomer product comprises $C_4+$ hydrocarbons and any suitable total amount of $C_6$ olefins and $C_8$ olefins, e.g., at least 50 wt. %, at least 65 wt. %, at least 75 wt. %, at least 80 wt. %, at least 82 wt. %, or at least 85 wt. %.

Aspect 8. The process defined in any one of the preceding aspects, wherein hydrogen in present in step (I), and the reaction mixture (or the effluent stream) comprises any suitable amount of hydrogen, e.g., from greater than 0 to 250 ppm, from greater than 0 to 100 ppm, or from 10 to 75 ppm (by weight).

Aspect 9. The process defined in any one of the preceding aspects, wherein the reaction mixture (or the effluent stream) comprises suitable amount of activated or deactivated catalyst system components, e.g., from 10 to 1000 ppm, from 20 to 500 ppm, or from 20 to 250 ppm (by weight).

Aspect 10. The process defined in any one of the preceding aspects, wherein the oligomer product is formed at any suitable reaction temperature, e.g., from 60° C. to 115° C., from 70° C. to 100° C., or from 75° C. to 95° C.

Aspect 11. The process defined in any one of the preceding aspects, wherein the oligomer product is formed at any suitable reaction pressure, e.g., from 400 psig to 1500 psig, from 600 psig to 1300 psig, or from 700 to 1200 psig.

Aspect 12. The process defined in any one of the preceding aspects, wherein the process has any suitable ethylene conversion, e.g., from 40 to 80%, from 45 to 75%, or from 50 to 70%, based on the amount of ethylene entering the reactor system and the amount of ethylene in the effluent stream in the reactor discharge line.

Aspect 13. The process defined in any one of the preceding aspects, wherein the ethylene flow rate is adjusted in step (IV).

Aspect 14. The process defined in any one of the preceding aspects, wherein the catalyst system flow rate is adjusted in step (IV).

Aspect 15. The process defined in any one of the preceding aspects, wherein the reaction temperature is adjusted in step (IV).

Aspect 16. The process defined in any one of the preceding aspects, wherein the reaction pressure is adjusted in step (IV).

Aspect 17. The process defined in any one of the preceding aspects, wherein the step of correlating comprises any suitable technique for determining the ethylene concentration.

Aspect 18. The process defined in any one of the preceding aspects, wherein the standard comprises a calibration curve.

Aspect 19. The process defined in any one of the preceding aspects, wherein the reactor comprises a stirred tank reactor or a plug flow reactor.

Aspect 20. The process defined in any one of the preceding aspects, wherein the reactor comprises a loop reactor.

Aspect 21. The process defined in any one of the preceding aspects, wherein the ultrasonic flow meter comprises a length of pipe integrated into the reactor (or a length of pipe integrated into the reactor discharge line, and prior to any pressure relief).

Aspect 22. The process defined in any one of the preceding aspects, wherein the ultrasonic flow meter has the same ID as the reactor (or the same ID as the reactor discharge line).

Aspect 23. The process defined in any one of the preceding aspects, wherein the process utilizes any suitable linear velocity of the reaction mixture (or the effluent stream) through the ultrasonic flow meter, e.g. from 0.5 to 20 ft/sec, from 2 to 15 ft/sec, from 3 to 10 ft/sec, or from 3 to 8 ft/sec.

Aspect 24. An oligomerization reactor system comprising:

(A) a reactor configured to contact a catalyst system with ethylene, an organic reaction medium, and optional hydrogen under oligomerization conditions to produce an oligomer product;

(B) one or more reactor inlets configured to introduce the catalyst system, ethylene, and the organic reaction medium into the reactor;

(C) a reactor discharge line configured to withdraw an effluent stream containing the oligomer product from the reactor;

(D) an analytical system configured to determine an ethylene concentration in the reactor and/or in the reactor discharge line, the analytical system comprising an ultrasonic flow meter; and (E) a controller configured to control an ethylene flow rate of the ethylene into the reactor, a catalyst system flow rate of the catalyst system into the reactor, a reaction temperature, a reaction pressure, or any combination thereof, based on (or according to) the ethylene concentration determined by the analytical system.

Aspect 25. The system defined in aspect 24, wherein the one or more reactor inlets are further configured to introduce hydrogen into the reactor.

Aspect 26. The system defined in aspect 24 or 25, wherein the catalyst system comprises a heteroatomic ligand chromium compound complex and an organoaluminum compound, or a heteroatomic ligand, a chromium compound, and an organoaluminum compound.

Aspect 27. The system defined in any one of aspects 24-26, wherein the ultrasonic flow meter is integrated into the reactor.

Aspect 28. The system defined in aspect 27, wherein the ultrasonic flow meter comprises a length of pipe integrated into the reactor, wherein the ultrasonic flow meter has the same ID as the reactor.

Aspect 29. The system defined in any one of aspects 24-26, wherein the ultrasonic flow meter is integrated into the reactor discharge line.

Aspect 30. The system defined in aspect 29, wherein the ultrasonic flow meter comprises a length of pipe integrated into the reactor discharge line, wherein the ultrasonic flow meter has the same ID as the reactor discharge line.

Aspect 31. The system defined in any one of aspects 24-30, wherein the reactor comprises a loop reactor.

Aspect 32. The system defined in any one of aspects 24-31, wherein the controller comprises a processing unit.

Aspect 33. The process or system defined in any one of the preceding aspects, wherein the organic reaction medium comprises any suitable hydrocarbon reaction medium, e.g., cyclohexane.

We claim:

1. An oligomerization reactor system comprising:

(A) a reactor configured to contact a catalyst system with ethylene, an organic reaction medium, and optional hydrogen under oligomerization conditions to produce an oligomer product;

(B) one or more reactor inlets configured to introduce the catalyst system, ethylene, and the organic reaction medium into the reactor;

(C) a reactor discharge line configured to withdraw an effluent stream containing the oligomer product from the reactor;

(D) an analytical system configured to determine an ethylene concentration in the reactor and/or in the reactor discharge line, the analytical system comprising an ultrasonic flow meter; and (E) a controller configured to control an ethylene flow rate of the ethylene into the reactor, a catalyst system flow rate of the catalyst system into the reactor, a reaction temperature, a reaction pressure, or any combination thereof, based on the ethylene concentration determined by the analytical system.

2. The system of claim 1, wherein the ultrasonic flow meter is integrated into the reactor.

3. The system of claim 1, wherein the ultrasonic flow meter is integrated into the reactor discharge line.

4. The system of claim 1, wherein the reactor comprises a loop reactor.

5. The system of claim 1, wherein the reactor and the ultrasonic flow meter are configured to operate at a temperature in a range from 60° C. to 115° C. and a pressure in a range from 400 psig to 1500 psig.

6. The system of claim 1, wherein the one or more reactor inlets are further configured to introduce hydrogen into the reactor.

7. The system of claim 1, wherein the catalyst system comprises a heteroatomic ligand chromium compound complex and an organoaluminum compound, or a heteroatomic ligand, a chromium compound, and an organoaluminum compound.

8. The system of claim 1, wherein:
the ultrasonic flow meter is integrated into the reactor; and
the ultrasonic flow meter comprises a length of pipe integrated into the reactor, wherein the ultrasonic flow meter has a same inside diameter as the reactor.

9. The system of claim 1, wherein:
the ultrasonic flow meter is integrated into the reactor discharge line; and
the ultrasonic flow meter comprises a length of pipe integrated into the reactor discharge line, wherein the ultrasonic flow meter has a same inside diameter as the reactor discharge line.

10. The system of claim 1, wherein the organic reaction medium comprises an aliphatic hydrocarbon.

11. A process for operating an oligomerization reactor system, the process comprising:

(I) contacting ethylene, an organic reaction medium, optionally hydrogen, and a catalyst system comprising a heteroatomic ligand chromium compound complex and an organoaluminum compound, or a heteroatomic ligand, a chromium compound, and an organoaluminum compound, in a reactor within the oligomerization reactor system to form an oligomer product;

(II) discharging an effluent stream containing the oligomer product from the reactor through a reactor discharge line;

(III) determining an ethylene concentration in the reactor discharge line by:
 (i) flowing the effluent stream through an ultrasonic flow meter integrated into the reactor discharge line;
 (ii) determining a speed of sound in the effluent stream from the ultrasonic flow meter; and
 (iii) correlating the speed of sound to a standard to determine the ethylene concentration in the reactor discharge line; and (IV) adjusting an ethylene flow rate of the ethylene into the reactor, a catalyst system flow rate of the catalyst system into the reactor, a reaction temperature, a reaction pressure, or any combination thereof, when the ethylene concentration has reached a predetermined level;

wherein the ultrasonic flow meter comprises a length of pipe integrated into the reactor discharge line.

12. The process of claim 11, wherein:
the process has an ethylene conversion in a range from 40 to 80 mol %; and
a linear velocity of the effluent stream through the ultrasonic flow meter is in a range from 0.5 to 20 ft/sec.

13. The process of claim 11, wherein the effluent stream comprises ethylene, the organic reaction medium, optionally hydrogen, the oligomer product, and activated or deactivated catalyst system components.

14. The process of claim 13, wherein the effluent stream contains:
from 6 to 25 wt. % ethylene;
from 40 to 70 wt. % organic reaction medium; and
from 15 to 30 wt. % oligomer product.

15. The process of claim 14, wherein the oligomer product contains $C_4+$ hydrocarbons and a total amount of $C_6$ olefins and $C_8$ olefins of at least 65 wt. %, based on the oligomer product.

16. The process of claim 11, wherein the oligomer product is formed at:
a reaction temperature in a range from 60° C. to 115° C.; and
a reaction pressure in a range from 400 psig to 1500 psig.

17. The process of claim 16, wherein:
the reaction temperature is adjusted in step (IV); or
the reaction pressure is adjusted in step (IV); or
both.

18. The process of claim 11, wherein:
the ethylene flow rate is adjusted in step (IV); or
the catalyst system flow rate is adjusted in step (IV); or
both.

19. The process of claim 11, wherein the standard comprises a calibration curve.

20. The process of claim 11, wherein the step of correlating comprises a mathematical model.

21. The process of claim 11, wherein the reactor comprises a loop reactor.

22. The process of claim 11, wherein the reactor comprises a stirred tank reactor.

* * * * *